United States Patent
Guan et al.

(10) Patent No.: US 9,541,530 B2
(45) Date of Patent: Jan. 10, 2017

(54) METHOD AND SYSTEM OF DETERMINISTIC FATIGUE LIFE PREDICTION FOR ROTOR MATERIALS

(71) Applicants: Xuefei Guan, Princeton, NJ (US); Hui Zhen, Zhangjiajie (CN); Jingdan Zhang, Plainsboro, NJ (US); Shaohua Kevin Zhou, Plainsboro, NJ (US); Ashley L. Lewis, Oviedo, FL (US); Steve H. Radke, Orlando, FL (US); Chin-Sheng Lee, Winter Springs, FL (US)

(72) Inventors: Xuefei Guan, Princeton, NJ (US); Hui Zhen, Zhangjiajie (CN); Jingdan Zhang, Plainsboro, NJ (US); Shaohua Kevin Zhou, Plainsboro, NJ (US); Ashley L. Lewis, Oviedo, FL (US); Steve H. Radke, Orlando, FL (US); Chin-Sheng Lee, Winter Springs, FL (US)

(73) Assignee: Siemens Energy, Inc., Orlando, FL (US)

( * ) Notice: Subject to any disclaimer, the term of this patent is extended or adjusted under 35 U.S.C. 154(b) by 639 days.

(21) Appl. No.: 13/743,601

(22) Filed: Jan. 17, 2013

(65) Prior Publication Data

US 2013/0191039 A1 Jul. 25, 2013

Related U.S. Application Data

(60) Provisional application No. 61/589,426, filed on Jan. 23, 2012.

(51) Int. Cl.
*G01N 29/34* (2006.01)
*G06F 17/00* (2006.01)
*G01N 17/00* (2006.01)

(52) U.S. Cl.
CPC .............. *G01N 29/34* (2013.01); *G01N 17/00* (2013.01); *G06F 17/00* (2013.01)

(58) Field of Classification Search
CPC ..................................................... G01N 29/34
See application file for complete search history.

(56) References Cited

U.S. PATENT DOCUMENTS 2,861,040 A 11/1958 Buchanan et al.
5,140,528 A * 8/1992 Swaminathan et al. ........ 702/34
(Continued)

FOREIGN PATENT DOCUMENTS

CN 1979112 A 6/2007
JP 2003322593 A 11/2003
(Continued)

OTHER PUBLICATIONS

Liu, Y., et al.; "Probabilistic Fatigue Life Prediction Using an Equivalent Initial Flaw Size Distribution"; 2009; GB; Mar. 1, 2009.
(Continued)

*Primary Examiner* — Manuel Rivera Vargas

(57) ABSTRACT

A method of fatigue life prediction including: calculating a critical crack size of an object of interest; identifying a first flaw in ultrasound data of the object of interest; determining that the first flaw interacts with a second flaw, the first flaw is to be merged with the second flaw, or the first flaw is isolated; calculating an initial crack size based on the determination; and calculating an increase in the initial crack size due to fatigue and creep to determine a number of load cycles until the initial crack size reaches the critical crack size.

21 Claims, 18 Drawing Sheets

(a) Crack-crack interaction

(56) References Cited

U.S. PATENT DOCUMENTS

| | | |
|---|---|---|
| 7,162,373 B1 | 1/2007 | Kadioglu et al. |
| 2005/0029893 A1 | 2/2005 | Baumann |
| 2010/0088261 A1 | 4/2010 | Montalvo |
| 2011/0068643 A1 | 3/2011 | Emery |
| 2013/0191039 A1 | 7/2013 | Guan et al. |

FOREIGN PATENT DOCUMENTS

| | | |
|---|---|---|
| JP | 2006064652 A | 3/2006 |
| JP | 2007256042 A | 10/2007 |
| JP | 2010216983 A | 9/2010 |
| KR | 0151852 B1 | 1/1998 |
| WO | 2013/112522 | 8/2013 |

OTHER PUBLICATIONS

International Search Report dated Apr. 23, 2013.
Yan-Shin Shih et al., "The stress intensity factor study of an elliptical cracked shaft", Nuclear Engineering and Design vol. 214 No. 1-2, pp. 137-145.
Canadian Report of Examination: Application No: 2861040; Filing Date: Jan. 23, 2013; (7 pages).
Japanese Report of Examination: Application No: 2014-553525; Filing Date: Jan. 23, 2013 (9 pages).
Liu, Y., et al.; "Probabilistic Fatigue Life Prediction Using an Equivalent Initial Flaw Size Distribution"; 2009.
Report of Examination mailed Jan. 26, 2016; Application No. 10-2014-7023612; 36 pages.

\* cited by examiner (a) Crack-crack interaction

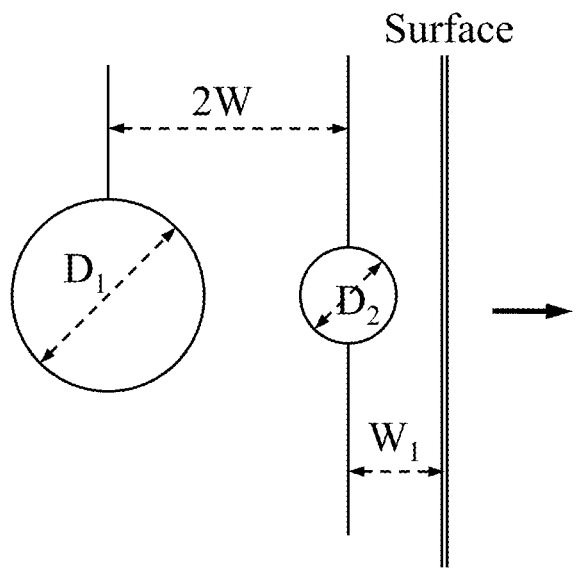
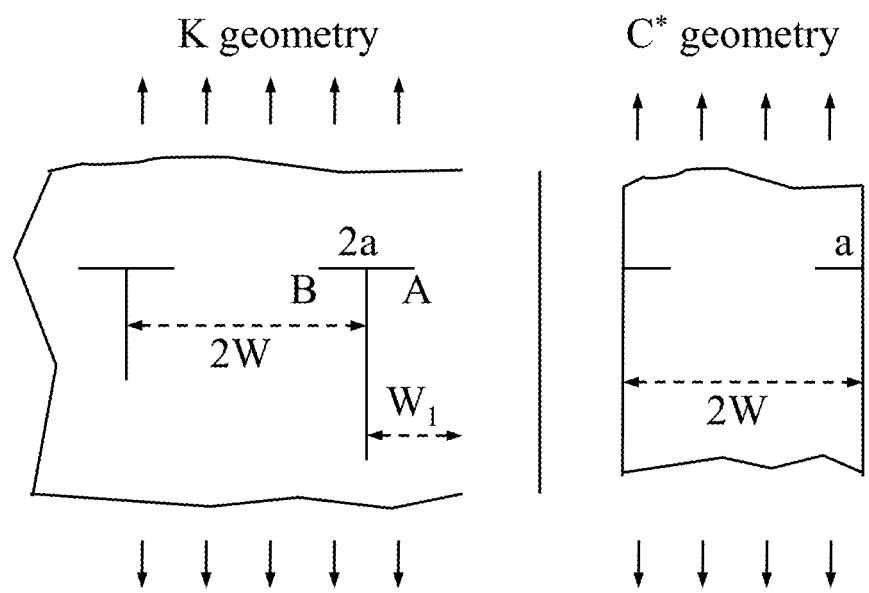
(b) Crack-crack-surface interaction
FIG. 1B (c) Crack-surface interaction (d) No interaction z-direction view
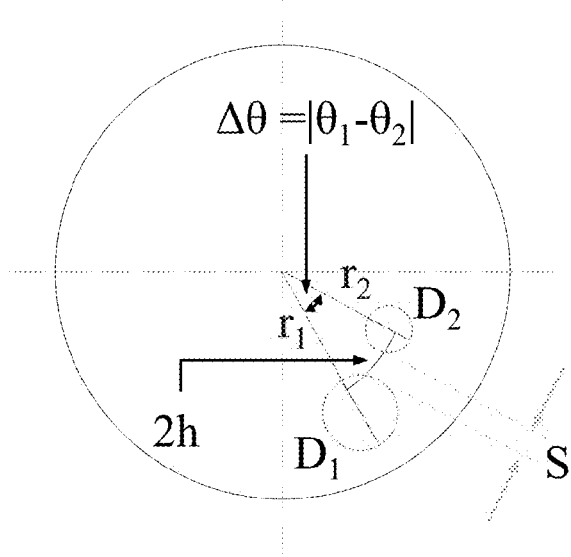
S is the spatial distance
D=max(D1,D2)
$2h \approx r_{ave}\Delta\theta$, with $r_{ave}=(r_1+r_2)/2$
If $2h/D < 0.8$ and $S<3D$
Interaction
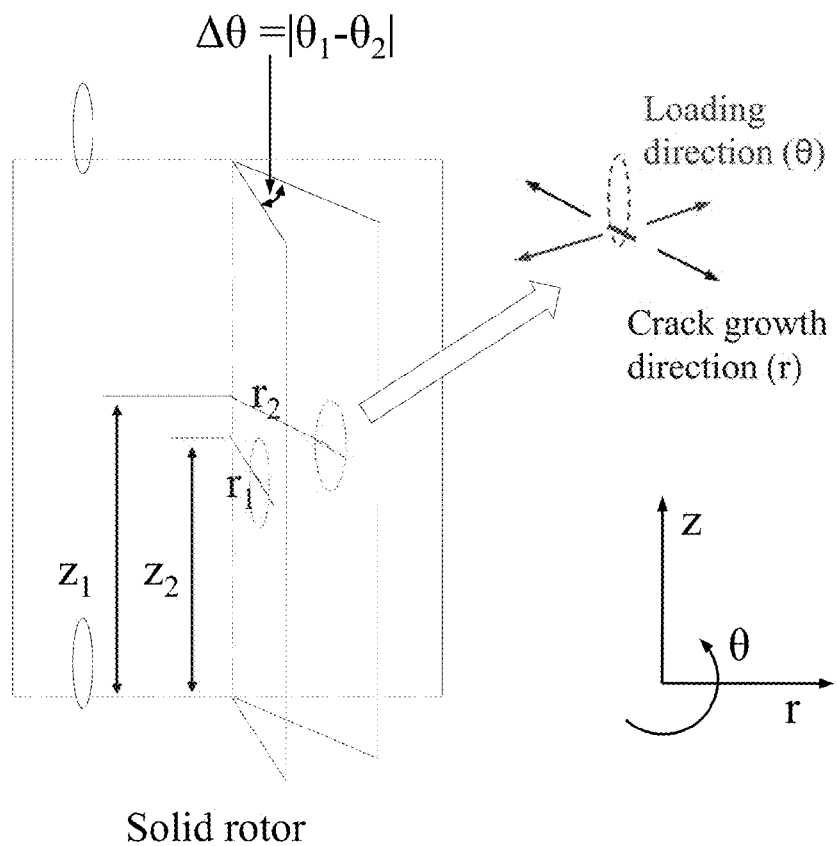
FIG. 2

S is the spatial distance
D=max(D1,D2)
If S/D ≤ 0.1, Merge into one crack
$D_{new}=D_1+D_2+S$ Table 1

| a/w | n=1 | n=2 | n3 | n5 | n7 | n10 | n13 | n=16 | n=20 |
|---|---|---|---|---|---|---|---|---|---|
| 0.000 | 4.59 | 7.13 | 9.60 | 14.98 | 21.40 | 33.96 | 51.39 | 75.76 | 123.4 |
| 0.125 | 4.57 | 6.17 | 7.38 | 9.04 | 10.80 | 12.88 | 14.88 | 16.64 | 19.52 |
| 0.250 | 4.40 | 5.28 | 5.52 | 6.60 | 7.00 | 7.28 | 7.44 | 7.56 | 7.68 |
| 0.375 | 4.29 | 4.88 | 5.12 | 5.12 | 4.90 | 4.48 | 3.97 | 3.52 | 2.99 |
| 0.500 | 4.44 | 4.86 | 4.96 | 4.86 | 4.64 | 4.24 | 3.82 | 3.20 | 3.02 |
| 0.625 | 5.06 | 5.41 | 5.52 | 5.47 | 5.24 | 4.80 | 4.06 | 3.78 | 3.63 |
| 0.750 | 6.99 | 8.39 | 9.56 | 11.25 | 12.61 | 14.50 | 15.87 | 15.07 | 23.20 |
| 0.875 | 16.22 | 28.34 | 44.57 | 89.60 | 160.0 | 389.7 | 888.0 | 1794.0 | 4366.0 |

Table 2

| a/w | n=1 | n=2 | n3 | n5 | n7 | n10 | n13 | n=16 | n=20 |
|---|---|---|---|---|---|---|---|---|---|
| 0.000 | 3.14 | 4.44 | 5.44 | 7.02 | 8.31 | 9.93 | 11.33 | 12.57 | 14.05 |
| 0.125 | 2.80 | 3.61 | 4.06 | 4.35 | 4.33 | 4.02 | 3.56 | 3.06 | 2.46 |
| 0.250 | 2.54 | 3.01 | 3.21 | 3.29 | 3.18 | 2.92 | 2.63 | 2.34 | 2.03 |
| 0.375 | 2.34 | 2.62 | 2.65 | 2.51 | 2.28 | 1.97 | 1.46 | 1.46 | 1.19 |
| 0.500 | 2.21 | 2.29 | 2.20 | 1.97 | 1.76 | 1.52 | 1.16 | 1.16 | 0.0978 |
| 0.625 | 2.12 | 1.96 | 1.76 | 1.43 | 1.17 | 0.863 | 0.458 | 0.458 | 0.300 |
| 0.750 | 2.07 | 1.73 | 1.47 | 1.11 | 0.895 | 0.642 | 0.461 | 0.337 | 0.216 |
| 0.875 | 2.08 | 1.64 | 1.40 | 1.14 | 0.987 | 0.814 | 0.688 | 0.573 | 0.461 |

FIG. 12

| | Expression | T(F°) | Material |
|---|---|---|---|
| E(ksi) | $31060-6.927T+1.323 \times 10^{-2}T^2-1.221 \times 10^{-5}T^3$<br>$31060-6.927T+1.323 \times 10^{-2}T^2-1.221 \times 10^{-5}T^3$<br>29000<br>30000 | $75 \leq T \leq 1000$<br>$75 \leq T \leq 500$<br>$>500$<br>75 | CrMoV<br>NiMoV-1,NiCrMoV-1,-2,-3<br>NiMoV-2,-3,NiCrMoV-4 |
| (ksi) | $95.94-5.68 \times 10^{-2}T+9.211 \times 10^{-5}T^2-6.413 \times 10^{-8}T^3$<br>$111.9-8.44 \times 10^{-2}T+2.905 \times 10^{-4}T^2-3.782 \times 10^{-7}T^3$<br>84.0<br>$105.4-0.1054T+7.61 \times 10^{-5}T^2+7.399 \times 10^{-8}T^3$<br>$125.9-0.1295T+3.522 \times 10^{-4}T^2-3.535 \times 10^{-7}T^3$<br>$130.8-3.928 \times 10^{-2}T+4.064 \times 10^{-5}T^2-8.838 \times 10^{-8}T^3$<br>100.0 | $75 \leq T \leq 1000$<br>$75 \leq T \leq 1000$<br>75<br>$75 \leq T \leq 500$<br>$75 \leq T \leq 500$<br>$75 \leq T \leq 500$<br>75 | CrMoV<br>NiMoV-1<br>NiMoV-2,-3<br>NiCrMoV-1<br>NiCrMoV-2<br>NiCrMoV-3<br>NiCrMoV-4 |
| | $81.73-0.9T+7.37 \times 10^{-3}T^2-1.24 \times 10^{-5}T^3$<br>140.0<br>$29.9+0.084T+6.67 \times 10^{-4}T^2$<br>115.0<br>$36.04-0.013T+8.46 \times 10^{-4}T^2$<br>107.0<br>$58.76-0.39T+4.02 \times 10^{-3}T^2-6.13 \times 10^{-6}T^3$<br>140.0<br>$40.88+1.18T-2.14 \times 10^{-3}T^2$<br>205 | $75 \leq T \leq 300$<br>$>300$<br>$75 \leq T \leq 300$<br>$>300$<br>$75 \leq T \leq 300$<br>$>300$<br>$75 \leq T \leq 300$<br>$>300$<br>$75 \leq T \leq 300$<br>$>300$ | CrMoV (new)<br>CrMoV (old)<br>NiMoV-1<br>NiMoV-2<br>NiCrMoV |
| $C_0$ | $(0.66+0.0009T) \times 10^{-9}$<br>$[1.11+0.00158(T-500)] \times 10^{-9}$ | $<500$<br>$500 \leq T \leq 1000$ | All |
| A | $5.95 \times 10^{-18} \exp\{85009/1460-85009/(T+460)\}$<br>$5.04 \times 10^{-23} \exp\{85009/1460-85009/(T+460)\}$ | | CrMoV (new)<br>CrMoV (old) |

FIG. 13

METHOD AND SYSTEM OF DETERMINISTIC FATIGUE LIFE PREDICTION FOR ROTOR MATERIALS

CROSS-REFERENCE TO RELATED APPLICATION

This application claims priority under 35 U.S.C. §119 to U.S. provisional application No. 61/589,426 filed Jan. 23, 2012, the disclosure of which is incorporated by reference herein in its entirety.

BACKGROUND OF THE INVENTION

1. Technical Field

The present invention relates to fatigue life prediction in rotor materials.

2. Discussion of the Related Art

Fatigue life prediction is an important management task in turbine generators. The casing, valves, and rotor materials are metallurgically degraded under long-term operation in an elevated temperature and high-pressure environment. Cracks due to fracture and creep may initiate and develop in years of service under severe conditions. Reliable life prediction techniques have been desired in the field for maintenance and repair plans to reduce the life-cycle cost.

Despite efforts made over the past decades, several difficulties and challenges remain in the field. Fatigue crack propagation in an elevated temperature and high-pressure environment is a complex and dynamic process, which involves many fields of expertise and empirical judgments. Two major components must be carefully included in fatigue life prediction under the severe environment: (1) time- and temperature-dependent fatigue and creep-fatigue crack growth, and (2) multiple crack interactions and their impact on final fatigue life. Fatigue crack growth is not only driven by the stress intensity factor but also by the J-integral. The interaction among multiple cracks or between cracks and boundaries affects the stress intensity factor and J-integral. The holding time in a typical loading profile for stream or gas turbines also affects fatigue crack growth. It is not easy for ordinary engineers without expertise to successfully perform life prediction.

A system that can manage useful and empirical information required in this process is desired.

SUMMARY OF THE INVENTION

In an exemplary embodiment of the present invention, a method of fatigue life prediction includes: calculating a critical crack size of an object of interest; identifying a first flaw in ultrasound data of the object of interest; determining that the first flaw interacts with a second flaw, the first flaw is to be merged with the second flaw, or the first flaw is isolated; calculating an initial crack size based on the determination; and calculating an increase in the initial crack size due to fatigue and creep to determine a number of load cycles until the initial crack size reaches the critical crack size.

The object of interest includes part of a turbine generator. The part includes a rotor. The first flaw interacts with the second flaw when a predetermined criteria for interaction is met. The first flaw is to be merged with the second flaw when a predetermined criteria for merging is met.

The step of calculating the increase in the initial crack size due to fatigue and creep is repeated until the initial crack size meets or exceeds the critical crack size.

A load cycle includes a minimum stress applied to the object, a maximum stress applied to the object, a temperature exposure of the object and a holding time.

In an exemplary embodiment of the present invention, a system of fatigue life prediction includes: a memory device for storing a program; a processor in communication with the memory device, the processor operative with the program to: calculate a critical crack size of an object of interest; identify a first flaw in ultrasound data of the object of interest; determine that the first flaw interacts with a second flaw, the first flaw is to be merged with the second flaw, or the first flaw is isolated; calculate an initial crack size based on the determination; and calculate an increase in the initial crack size due to fatigue and creep to determine a number of load cycles until the initial crack size reaches the critical crack size.

The object of interest includes part of a turbine generator. The part includes a rotor. The first flaw interacts with the second flaw when a predetermined criteria for interaction is met. The first flaw is to be merged with the second flaw when a predetermined criteria for merging is met.

The processor is further operative with the program code to repeat calculating the increase in the initial crack size due to fatigue and creep until the initial crack size meets or exceeds the critical crack size.

In an exemplary embodiment of the present invention, a computer program product for fatigue life prediction includes: a non-transitory computer readable storage medium having computer readable program code embodied therewith, the computer readable program code comprising: computer readable program code configured to perform the steps of: calculating a critical crack size of an object of interest; identifying a first flaw in ultrasound data of the object of interest; determining that the first flaw interacts with a second flaw, the first flaw is to be merged with the second flaw, or the first flaw is isolated; calculating an initial crack size based on the determination; and calculating an increase in the initial crack size due to fatigue and creep to determine a number of load cycles until the initial crack size reaches the critical crack size.

The object of interest includes part of a turbine generator. The part includes a rotor. The first flaw interacts with the second flaw when a predetermined criteria for interaction is met. The first flaw is to be merged with the second flaw when a predetermined criteria for merging is met.

The step of calculating the increase in the initial crack size due to fatigue and creep is repeated until the initial crack size meets or exceeds the critical crack size.

In an exemplary embodiment of the present invention, a method of fatigue life prediction includes: calculating a critical crack size of an object of interest; identifying a first flaw of the object of interest; determining that the first flaw interacts with a second flaw, the first flaw is to be merged with the second flaw, or the first flaw is isolated; calculating an initial crack size based on the determination; and calculating an increase in the initial crack size due to fatigue and creep to determine a number of load cycles until the initial crack size reaches the critical crack size.

The first and second flaws are found using non-ultrasound data.

BRIEF DESCRIPTION OF THE DRAWINGS

FIGS. 1A-D illustrate crack tip (A and B) magnification factors for various geometry configurations;

FIG. 2 is an interaction illustration diagram;

Figure 5:
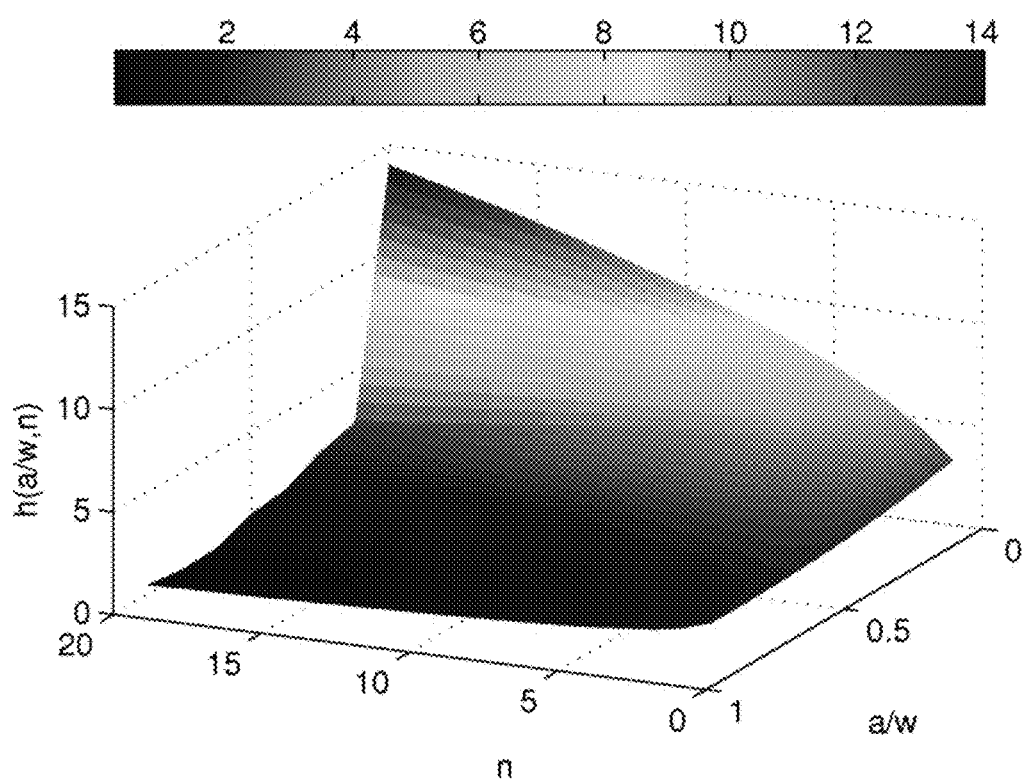
Figure 6:
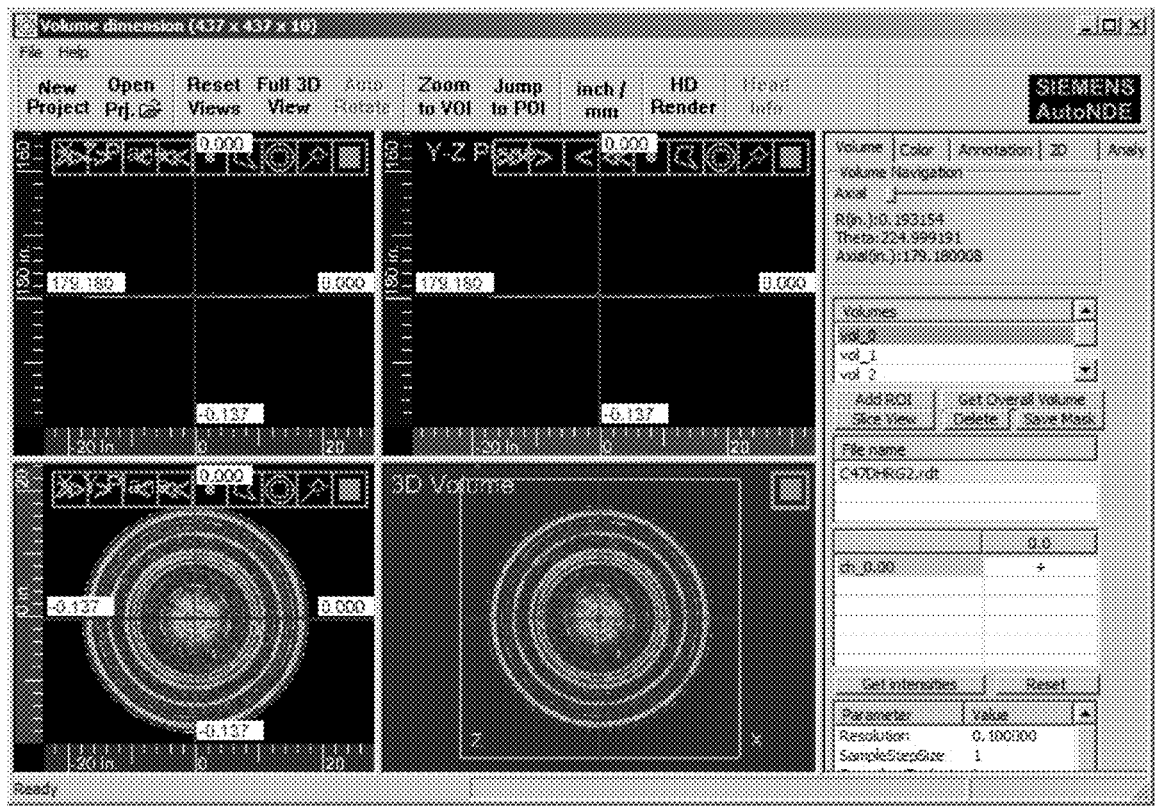
Figure 7:
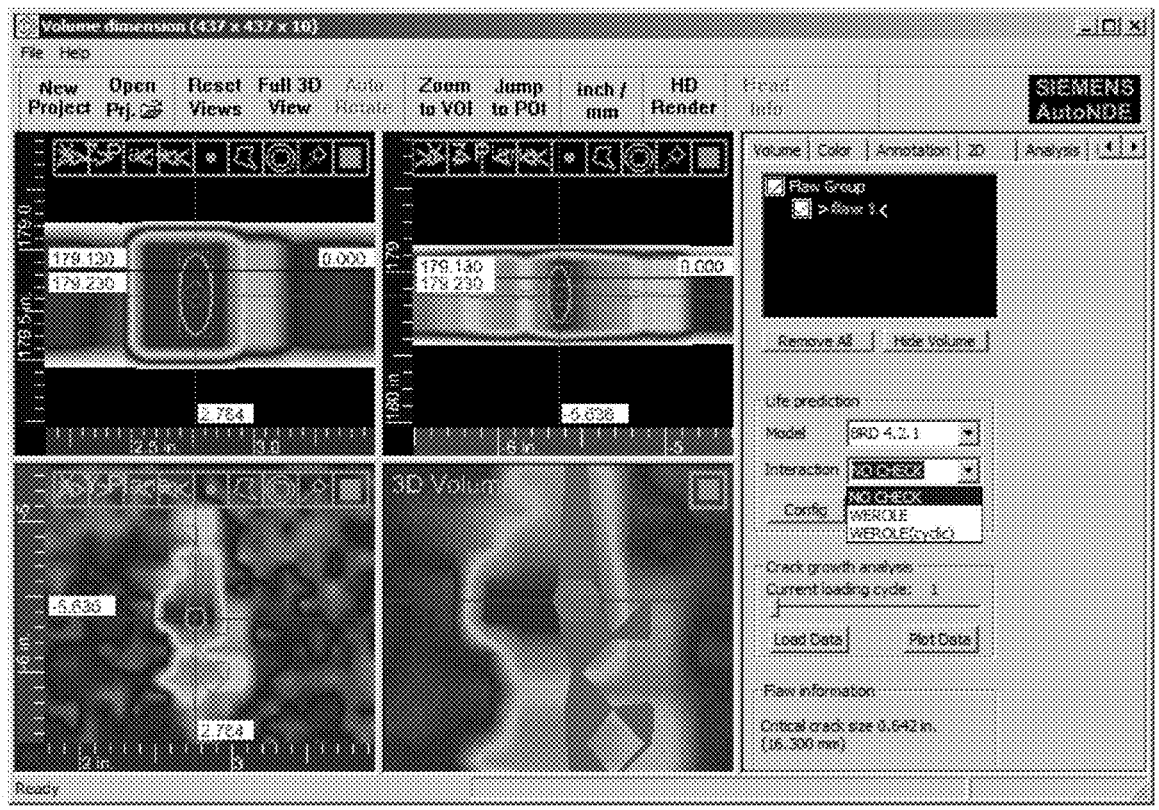
Figure 8:
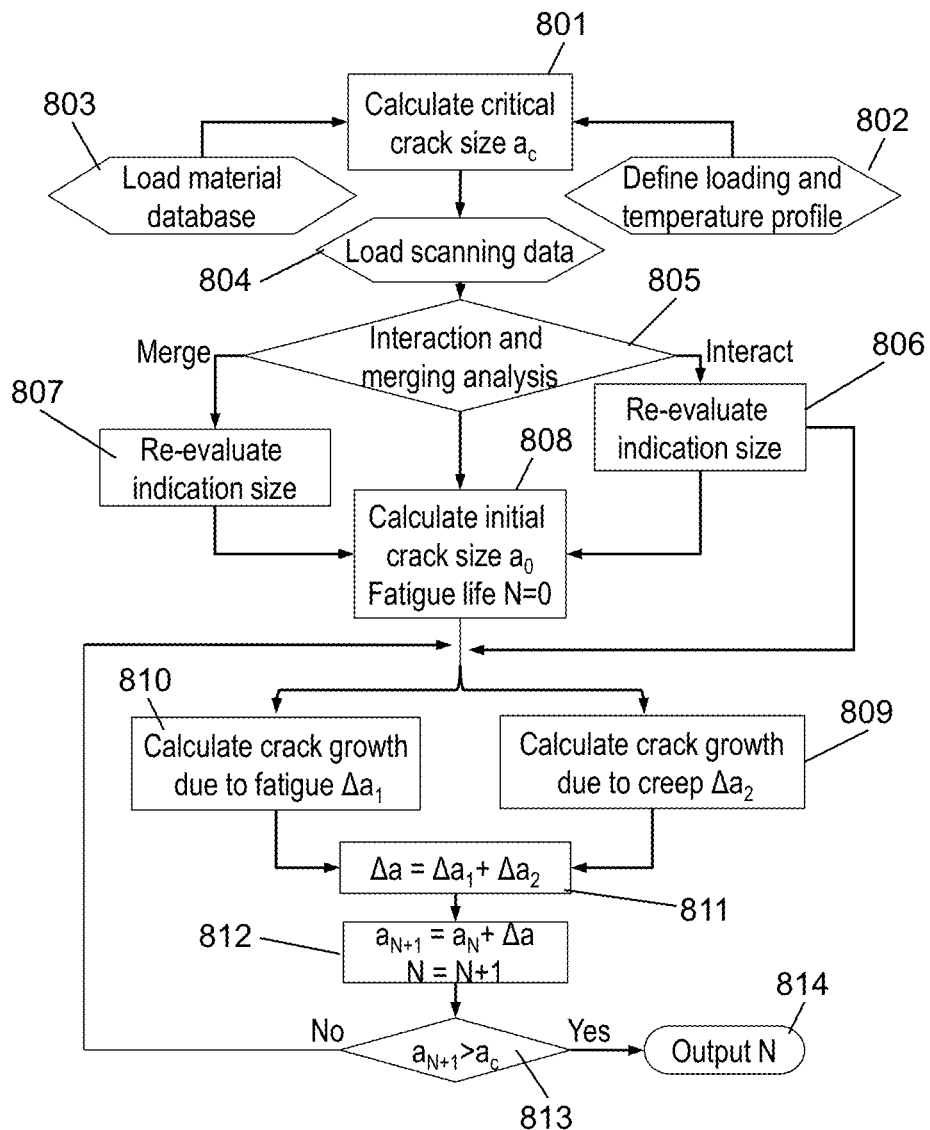
Figure 9A:
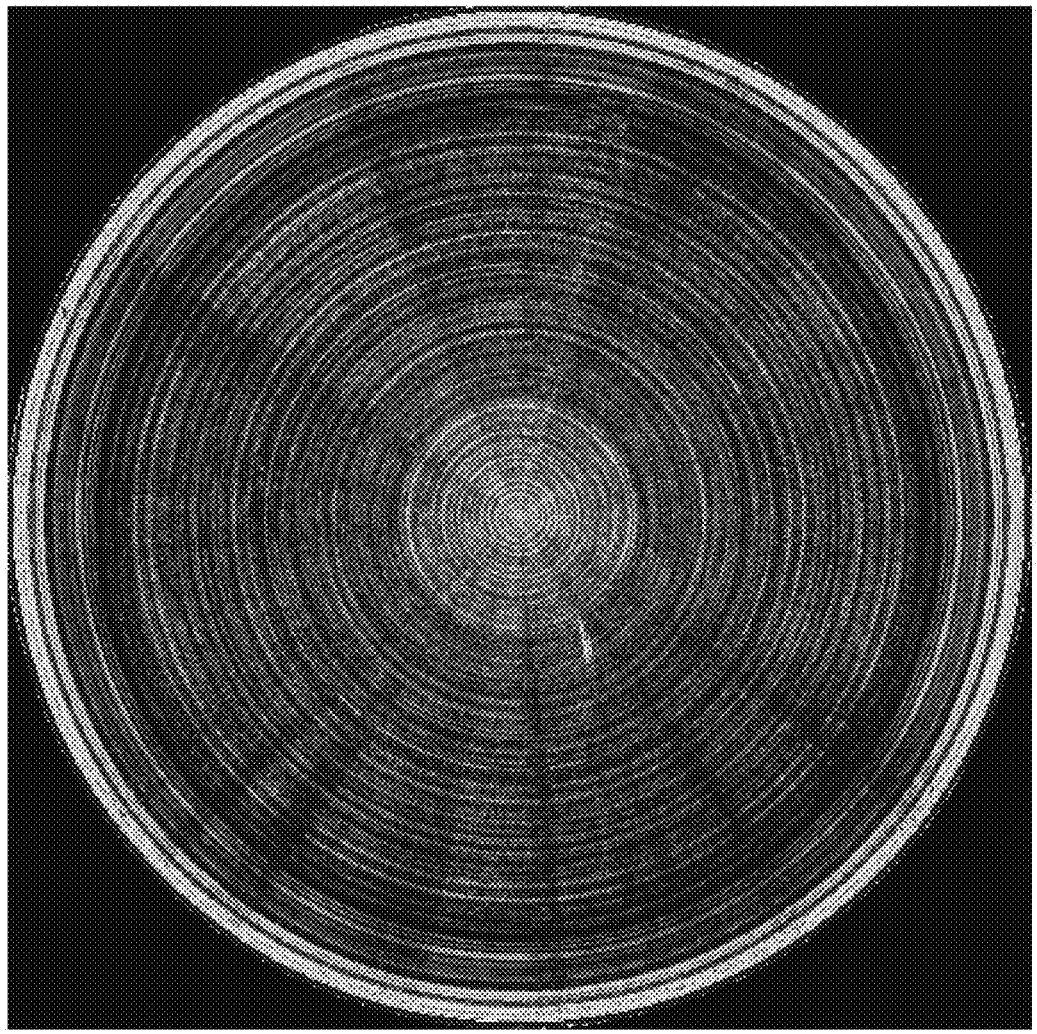
Figure 9B:
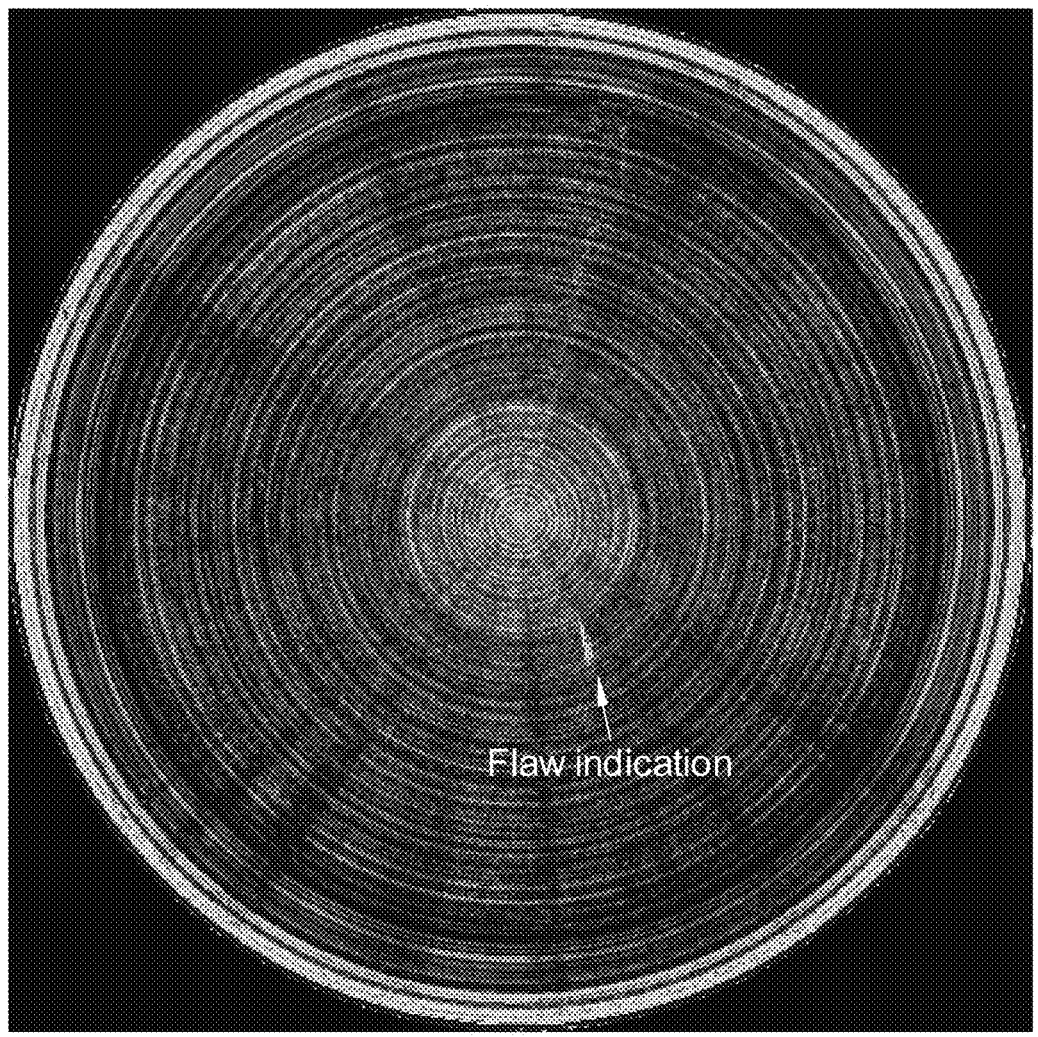
Figure 10:
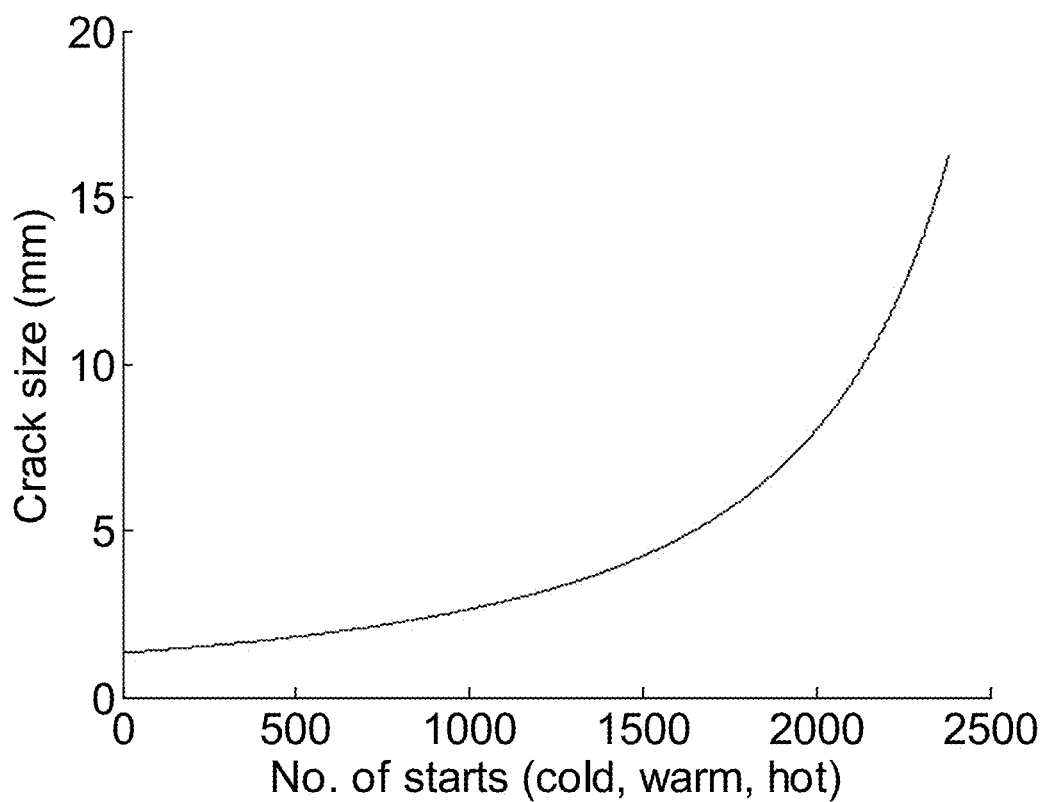
Figure 11:
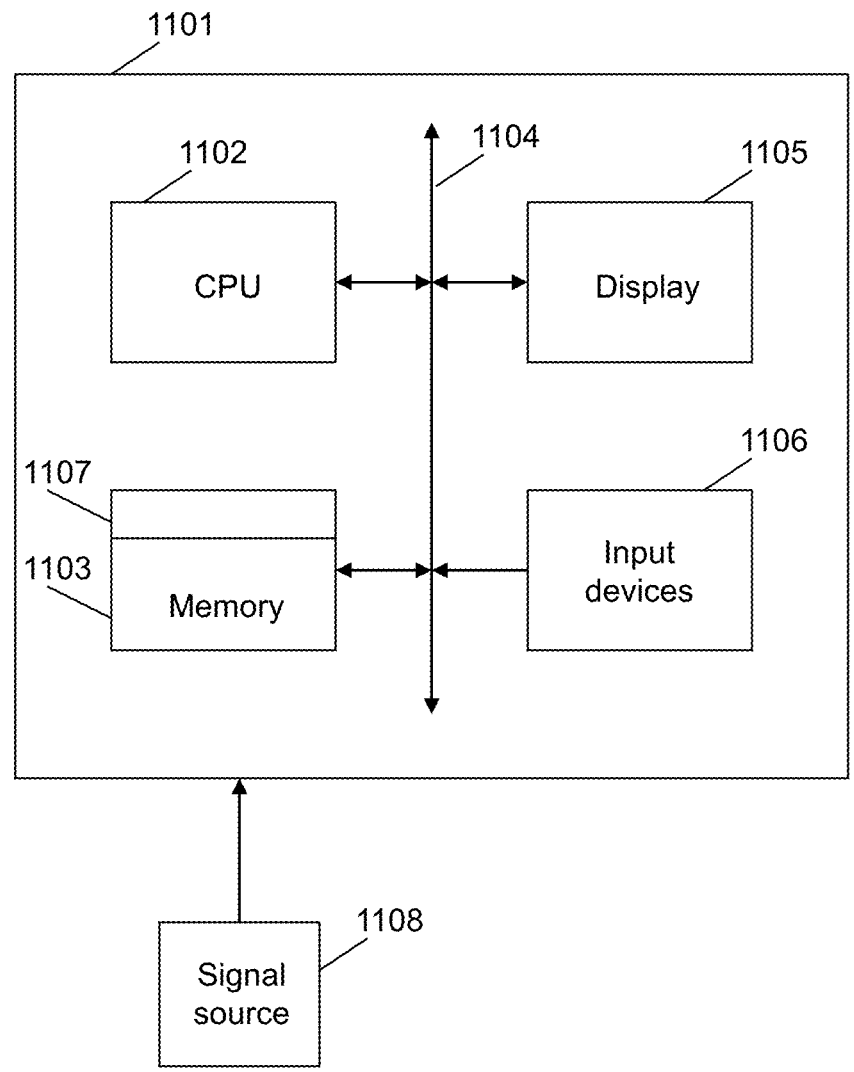

for double edge notched panel (DENO) in plain strain under remote tension;

FIG. 5 illustrates a response surface of $$h\left(\frac{a}{w}, n\right)$$

for center cracked panel (CCPL) in plain strain under remote tension;

FIG. 6 illustrates a system software platform, which may embody an exemplary embodiment of the present invention;

FIG. 7 illustrates a fatigue life prediction module in the system software platform of FIG. 6 according to an exemplary embodiment of the present invention;

FIG. 8 is a flowchart of crack growth and life calculation, according to an exemplary embodiment of the present invention;

FIGS. 9A-B illustrate response images calculated from ultrasound inspection data;

FIG. 10 is a graph illustrating fatigue crack growth trajectory of a flaw, calculated in accordance with an exemplary embodiment of the present invention;

FIG. 11 illustrates a computer system in which an exemplary embodiment of the present invention may be implemented;

FIG. 12 illustrates a pair of tables;

FIG. 13 illustrates a table; and

Figure 14:
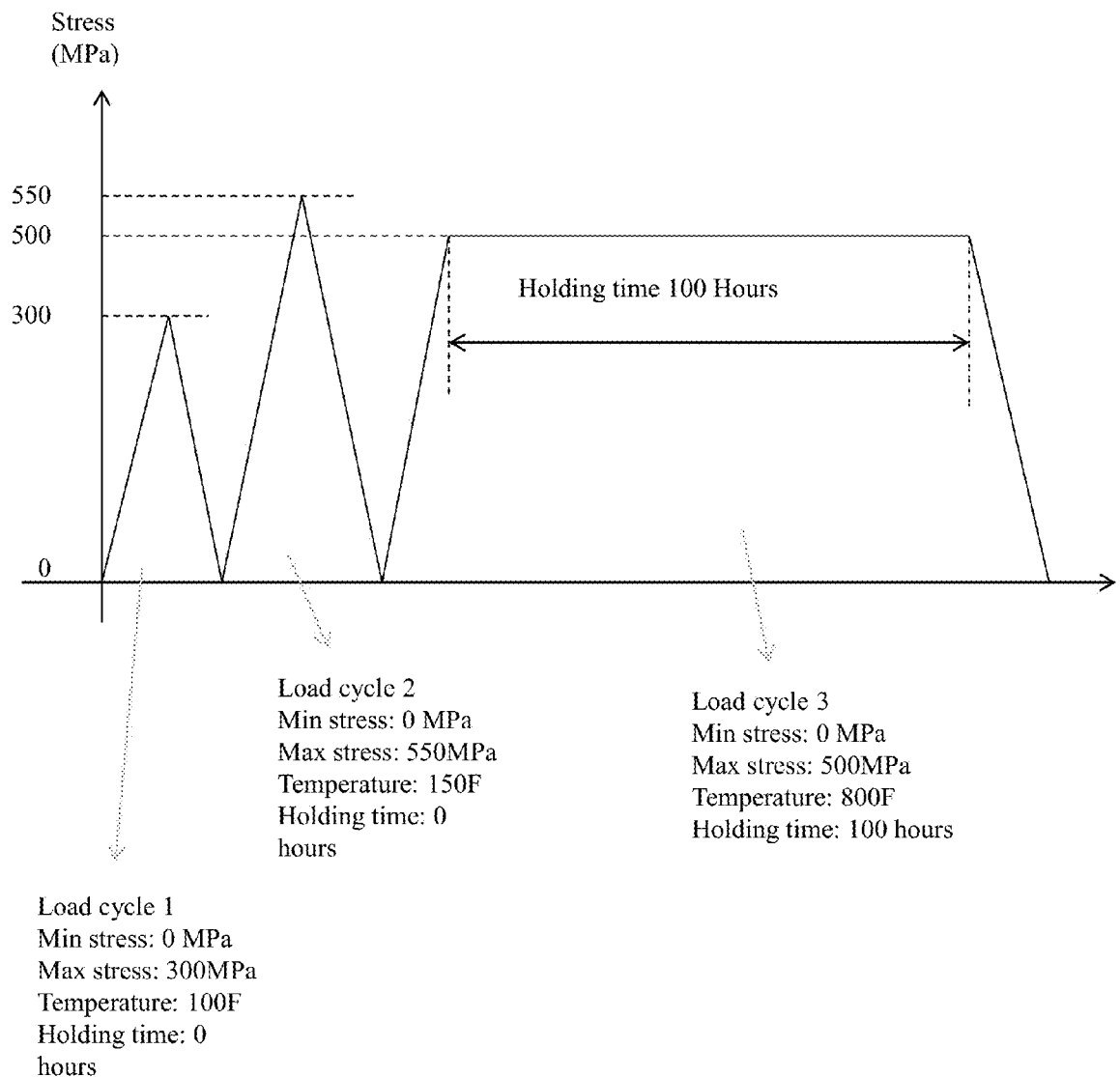

FIG. 14 illustrates three exemplary load cycles.

DETAILED DESCRIPTION OF EXEMPLARY EMBODIMENTS

According to an exemplary embodiment of the present invention, there is provided a methodology for time-dependent fatigue-creep fracture analysis. The methodology is based on fracture mechanics and plasticity, and is particularly designed for programming. The interaction between multiple cracks and the interaction between crack and rotor surface are systematically included. The methodology may be embodied in expert system software such as Siemens AutoNDE, which is implemented using Microsoft Visual Studio and has a mature three-dimensional (3D) visualization capability. The system directly supports non-destructive evaluation (NDE) testing data for probabilistic fatigue life prediction.

This disclosure is organized as follows. First, the theoretical foundation of time- and temperature-dependent fatigue crack propagation at elevated temperature is presented. In addition, deterministic analysis of fatigue life prediction using the developed model is presented. Second, interaction criteria for crack-crack and crack-surface situations are described, according to exemplary embodiments of the present invention. Next, the expert system AutoNDE with a module incorporating an exemplary embodiment of the present invention is introduced. Following this, examples are used to demonstrate the inventive methodology and expert system software. Finally, conclusions are presented.

General fatigue life prediction methodology.

The section presents the methodology of fatigue life prediction under elevated temperature as well as the creep-fatigue crack growth model, time- and temperature-dependencies of the crack propagation.

Fatigue crack growth model.

The crack size increment at elevated temperature is generally expressed as, $$\frac{da}{dN} = \left[\frac{da}{dN}\right]_{cyc} + \left[\frac{da}{dt}\right]_{ave} t_h, \quad (1)$$

where a is the crack size and N is the number of cyclic loads.

The first term accounts for the pure fatigue contribution. Paris' model in the following equation is one of the most commonly used models for the first term in Eq. (1).

$$\left[\frac{da}{dN}\right]_{cyc} = C_0 (\Delta K)^{n_0}, \quad (2)$$

where $C_0$ and $n_0$ are two model parameters estimated from experimental data. $\Delta K$ is the cyclic stress intensity range.

The second term of Eq. (1) accounts for the time-dependent creep or fatigue-creep contribution, $$\left[\frac{da}{dt}\right]_{ave}$$

is the average crack growth rate and $t_h$ is the holding time. $(C_t)_{ave}$ may be used to correlate time dependent crack growth for trapezoidal loading wave shapes. During a hold time, $t_h$, $(C_t)_{ave}$ is defined as $$(C_t)_{ave} = \frac{1}{t_h} \int_0^{t_h} h C_t dt. \quad (3)$$

The following expression for the $C_t$ parameter has been shown to characterize creep crack growth rates over a wide range of creep conditions.

$$C_t = (C_t)_{SSC} + C^*(t), \quad (4)$$

where $(C_t)_{SSC}$ represents the value of $(C_t)$ in the small scale creep (SSC) region and $C^*(t)$ characterizes the time dependent value of $C^*$ in the transition region between small scale creep and extensive creep conditions. Two general cases for elastic, plastic, and creep deformation are briefly introduced below.

Elastic, plastic, primary and secondary creep.

The elastic, plastic, primary and secondary creep deformation rates of rotor steels can be described by the following uni-axial constitutive equation.

$$\dot{\varepsilon} = \frac{\dot{\sigma}}{E} + A_1 \varepsilon^{-p} \sigma^{n_1(1+p)} + A\sigma^n, \quad (5)$$

where $A_1$, p, and $n_1$ are constants describing the primary creep and A and n are parameters describing the secondary creep. $\sigma$ is the stress. Expressions for estimating the value of $C_t$ for components which behave according to Eqs. (4) and (5) are given by $$(C_t)_{SSC} = 2(1-v^2)\beta\left(\frac{F'}{F}\right)\frac{K^2}{EW}\dot{r}_c, \quad (6)$$

and $$C^*(t) \approx \frac{C_h^*}{(1+p)t^{\frac{p}{1+p}}} + C^*, \quad (7)$$

where v is Poisson's ratio, E is elastic modulus, K is stress intensity, W is the width of the specimen, F is the geometry correction function, F' is the derivative of F with respect $$\frac{a}{W},$$

and $\dot{r}_c$ the rate of change of the creep zone given by $$\dot{r}_c = \frac{K^2}{2\pi}\left[\frac{I_{n1}E}{2\pi(1-v^2)}\right]^{\frac{2}{n_1-1}}[(1+p)(1+n_1)A_1] \quad (8)$$

$$\frac{2}{(1+p)(n_1-1)}\frac{2\tilde{r}_c(\theta)}{(1+p)(n_1-1)}t^{\frac{2}{(1+p)(n_1-1)}-1}.$$

From finite element analysis, $\beta$ is a scaling constant determined to be 0.33 and $\tilde{r}_c(\theta)=0.4$ is a non-dimensional constant of the crack tip stress field. Term $I_{n1}$ is a dimensionless function of the primary creep exponent.

$$I_{n1} = 6.568 - 0.4744n_1 + 0.0404n_1^2 - 0.001261n_1^3. \quad (9)$$

The value of $C^*_h$ can be obtained by substituting A with $[(1+p)A_1]^{1/(1+p)}$ and n with $n_1$ in the expression for $C^*$. With appropriate substitutions, an expression for $(C_1)_{ave}$ for materials which deform by elastic, plastic, primary and secondary creep can be obtained by integrating Eq. (4), $$(C_t)_{ave} = \frac{\beta \tilde{r}_c(\theta)}{\pi E}(1-v^2)\frac{\Delta K_h^4}{W t_h} \quad (10)$$

$$\frac{F'}{F}\left[\frac{I_{n1}E}{2\pi(1-v^2)}\right]^{\frac{2}{n_1-1}}[(1+p)(1+n_1)A_1]\frac{2}{(1+p)(n_1-1)} \times$$

$$\left[(t_h + t_{pl})^{\frac{2}{(1+p)(n_1-1)}} - t_{pl}^{\frac{2}{(1+p)(n_1-1)}}\right] + \frac{C_h^*}{t_h^{\frac{p}{1+p}}} + C^*.$$

$\Delta K_h$ is the stress intensity range of hold time. $t_{p1}$ is a time shift constant which accounts for creep retardation due to plasticity and can be estimated by $$t_{pl} = \frac{1}{(1+p+n_1)A_1}\left[\frac{2\pi(1-v^2)}{I_{n_1}E}\left[\xi\frac{2\pi}{\tilde{r}_c(\theta)}\frac{m-1}{m+1}\left(\frac{1}{2\sigma_y}\right)^2\right]^{\frac{n_1-1}{2}}\right]^{1+p}, \quad (11)$$

where $\xi \approx 0.55$ is a scaling constant from finite element analysis, $\sigma_y$ is the yield stress, and m is the cyclic plasticity exponent.

Elastic, plastic, and secondary creep only.

If primary creep behavior is not considered or assumed to be negligible, Eq. (5) reduces to $$\dot{\varepsilon} = \frac{\dot{\sigma}}{E} + A\sigma^n. \quad (12)$$

In this case, the creep zone expansion rate $\dot{r}_c$ in Eq. (4) is a function of the secondary creep constants A and n and is expressed as $$\dot{r}_c = \frac{2\alpha}{n-1}K^2 t^{-\frac{n-3}{n-1}}(EA)^{\frac{2}{n-1}}\tilde{r}_c(\theta). \quad (13)$$

$\alpha$ is a scaling factor and depends on n coming from the creep zone expansion rate expression. $\alpha$ is expressed as $$\alpha = \frac{1}{2\pi}\left[\frac{(n+1)^2}{2n\alpha_n^{n+1}}\right]^{\frac{2}{n-1}}, \quad (14)$$

where $\alpha_n^{n+1} = 0.69$ for $3 \leq n \leq 13$. The time dependent behavior of $C^*$ described by the term $C^*_h$ in Eq. (7) is not applicable. Thus for materials deforming by elastic, plastic and secondary creep, the expression for $(C_t)_{ave}$ has the following form $$(C_t)_{ave} = \quad (15)$$

$$\frac{2\alpha\beta\tilde{r}_c(\theta)}{E}(1-v^2)\frac{\Delta K_h^4}{W}\frac{F'}{F}(EA)^{\frac{2}{n-1}}\left[\frac{(t_h+t_{pl})^{\frac{2}{n-1}} - t_{pl}^{\frac{2}{n-1}}}{t_h}\right] + C^*.$$

The creep retardation time $t_{p1}$ in this case is given by $$t_{pl} = \frac{1}{EA}\left[\xi\frac{m-1}{m+1}\left(\frac{1}{2\sigma_y}\right)^2\frac{1}{\alpha\tilde{r}_c(\vartheta)}\right]^{\frac{n-1}{2}}. \quad (16)$$

Under pure creep conditions, $(C_t)_{ave}$ and $$\frac{da}{dt}$$

are correlated by $$\left[\frac{da}{dt}\right]_{ave} = B(C_t)_{ave}^q, \quad (17)$$

where B and q are two calibration parameters. Using Paris' equation for cycle dependent crack growth, Eq. (1) can be written as $$\frac{da}{dN} = C_0 \Delta K^{n_0} + B(C_t)_{ave}^q t_h. \quad (18)$$

Correction factors of geometry for stress intensity computation.

Figure 1A:
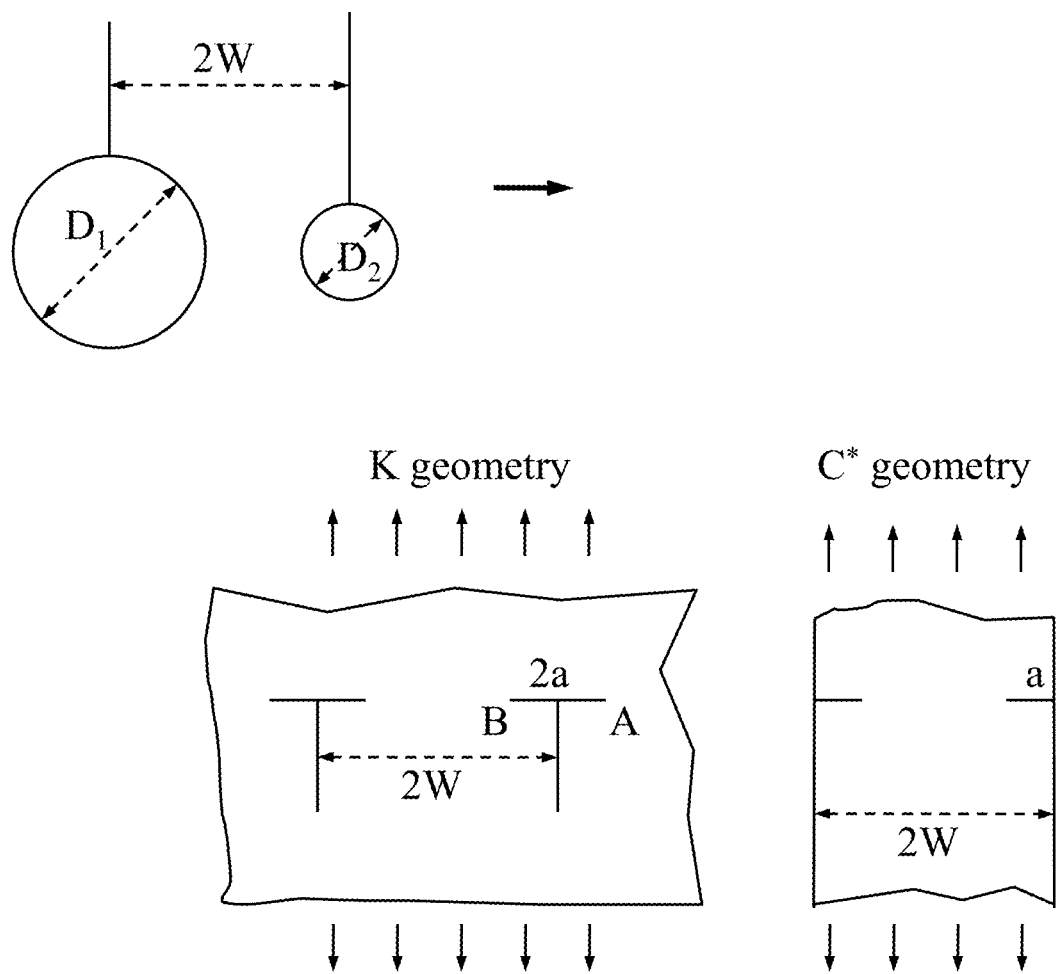
Figure 1C:
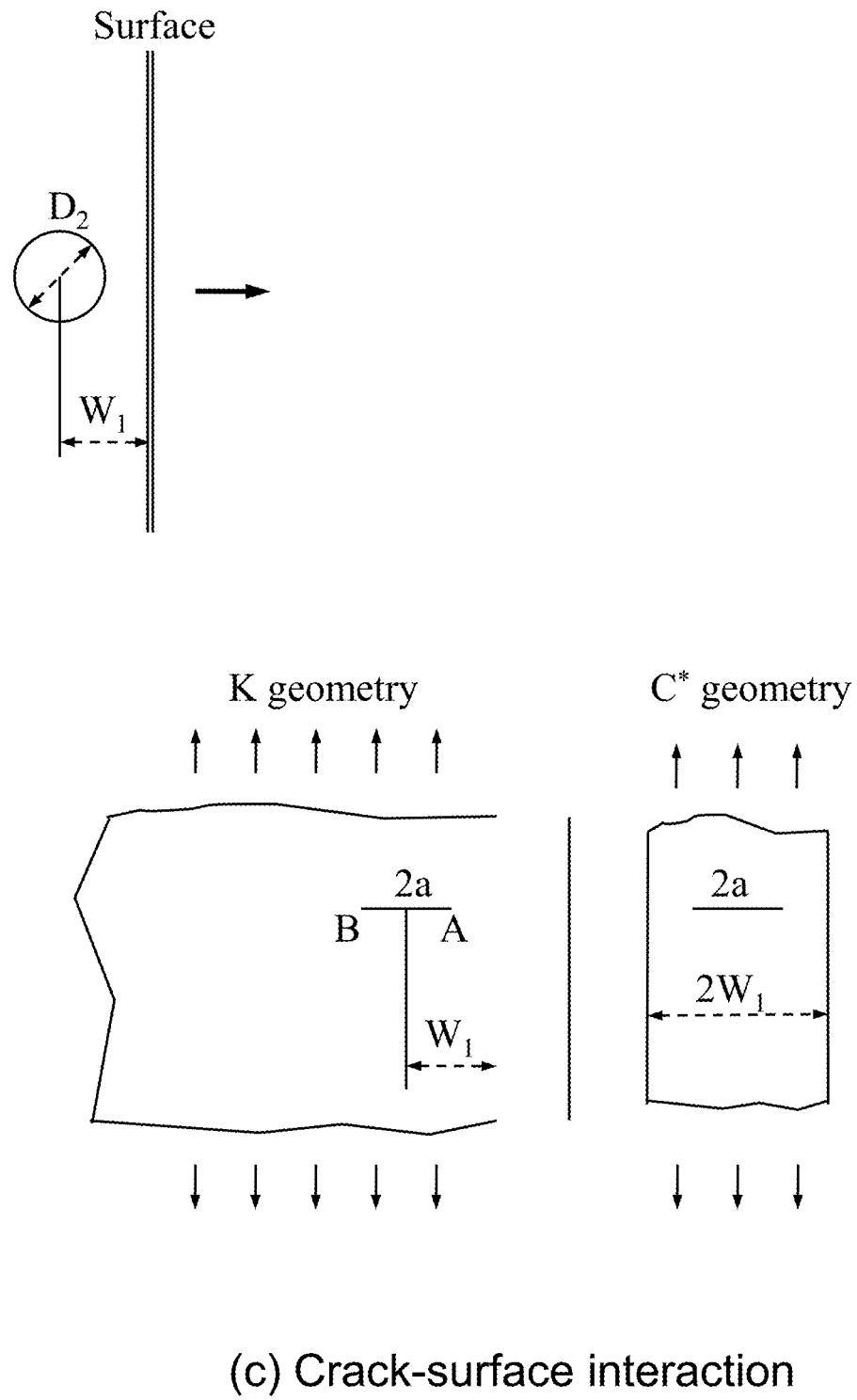
Figure 1D:
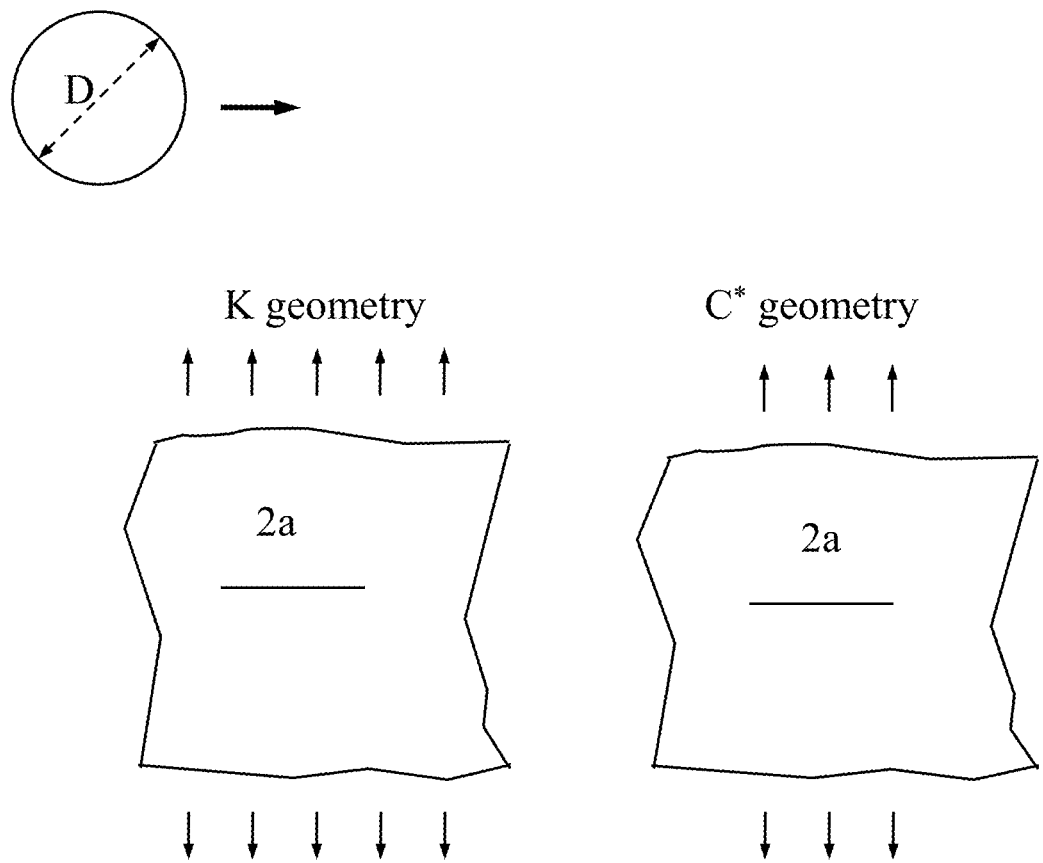

Four types of crack geometries shown in FIGS. 1A-D are used to represent NDE indications and interactions. $C^*$ expressions for each of these cases can be derived from fully plastic J-integral solutions. Geometry configurations in FIGS. 1A and 1B are modeled as double edge notched panels (DENO). The configuration in FIG. 1C is modeled as center cracked panel (CCPL). The configuration in FIG. 1D is modeled as an isolated or edge connected crack.

C* expressions for these four cases are shown in Eq. (19) with case (a,b), case (c) and case (d) in sequence.

$$C^* = \begin{cases} Aa\left(1 - \frac{a}{W}\right)h\left(\frac{a}{W}, n\right)\left[\frac{2\sigma}{0.72 + 1.82\left(1 - \frac{a}{W}\right)}\right]^{n+1} \\ C_1 A a \pi \sqrt{n} \left(\frac{\sqrt{3}}{2}\sigma\right)^{n+1} \\ \frac{Aah\left(\frac{a}{W}, n\right)}{\left(1 - \frac{a}{W}\right)^n}\left(\frac{\sqrt{3}}{2}\sigma\right)^{n+1} \end{cases} \quad (19)$$

The geometry correction function $$F\left(\frac{a}{W}\right)$$

in K calculation for these four cases is shown in Eq. (20) with case (a,b), case (c) and case (d) in sequence.

$$F\left(\frac{a}{W}\right) = \begin{cases} 1.122 - 0.561\left(\frac{a}{W}\right) - 0.205\left(\frac{a}{W}\right)^2 + 0.471\left(\frac{a}{W}\right)^3 - 0.19\left(\frac{a}{W}\right)^4 \\ 1.0 - 0.5\left(\frac{a}{W}\right) + 0.37\left(\frac{a}{W}\right)^2 - 0.044\left(\frac{a}{W}\right)^3 \\ 0.5\left(\frac{a}{W}\right) \end{cases} \quad (20)$$

Crack shape parameters Q and the location parameters $C_1$ for stress intensity computations are defined in the following equations. In Eq. (21), through thickness (isolated), non-through thickness (isolated), through-thickness (surface) and non-through thickness (surface) are in sequence. In Eq. (22), embedded cracks and surface cracks are in sequence.

$$Q = \begin{cases} 1.0 = 0.212\left(\frac{\sigma}{\sigma_y}\right)^2 \\ 1.0 + 4.594\left(\frac{a}{2c}\right)^{1.656} - 0.212\left(\frac{\sigma}{\sigma_y}\right)^2 \\ 1.0 \\ 1.0 + 4.594\left(\frac{a}{2c}\right)^{1.656} \end{cases} \quad (21)$$

and $$C_1 = \begin{cases} 1.0 \\ 1.12 \end{cases} \quad (22)$$

Figure 4:
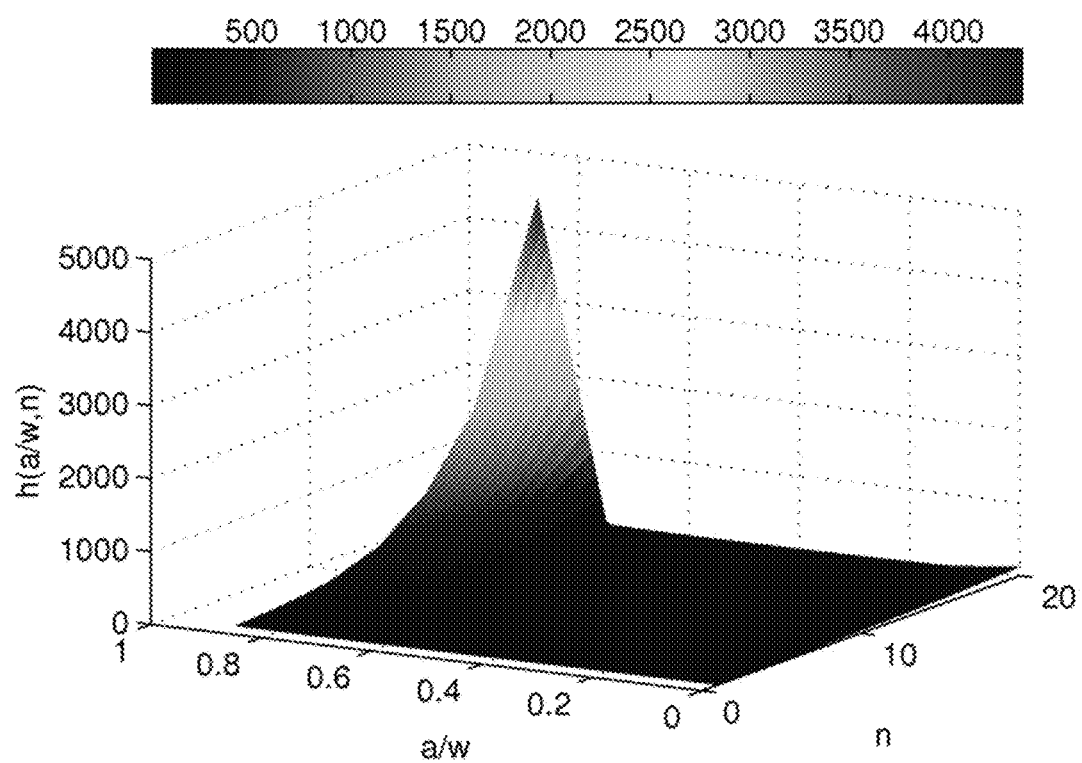
FIG. 4 illustrates a response surface of $$h\left(\frac{a}{w}, n\right)$$

The functions h(a/W,n) used in Eq. (19) are tabulated in Tables 1 and 2 (see FIG. 12) for DENO and CCPL types of specimens respectively. The corresponding surface plots for h(a/W,n) are shown in FIGS. 4 and 5. Given values of a/W and the creep exponent n, the function value of h(a/W,n) is interpolated using Tables 1 and 2.

Magnification factors of interaction for stress intensity computation.

The magnification factors for stress intensity calculation induced by crack-crack interactions and crack-surface interactions can be represented using the specimen geometry configuration in FIG. 1A. The following polynomial fitting functions may be used.

$$M_A = \begin{cases} 1.0 + 0.058\left(\frac{a}{W}\right) - 0.136\left(\frac{a}{W}\right)^2 + 0.247\left(\frac{a}{W}\right)^3 \\ \frac{1.0 + 0.649\left(\frac{a}{W}\right) + 0.714\left(\frac{a}{W}\right)^2 - 0.0661\left(\frac{a}{W}\right)^3}{\sqrt{1.0 - \frac{a}{W}}} \end{cases} \quad (23)$$

case (a); case (c)

$$M_B = \begin{cases} \frac{1.0 - 0.605\left(\frac{a}{W}\right) + 0.41\left(\frac{a}{W}\right)^2 - 0.465\left(\frac{a}{W}\right)^3}{\sqrt{1.0 - \frac{a}{W}}} \\ 1.0 + 0.0648\left(\frac{a}{W}\right) - 0.0339\left(\frac{a}{W}\right)^2 + 0.24\left(\frac{a}{W}\right)^3 \end{cases} \quad (24)$$

case (a); case (c)

To account for the influence on a free surface on two interacting cracks as shown in FIG. 1B, the corresponding magnification factors may be multiplied for each case.

Temperature-dependent parameters.

Creep-fatigue is both time-dependent and temperature-dependent. The time-dependency has been constructed in Eq. (17). Many of the temperature-dependent parameters can be obtained using creep testing. The temperature-dependent parameters are listed in Table 3 (see FIG. 13).

Deterministic remaining useful life prediction.

The remaining useful life estimate involves computations of the initial crack size $a_0$ extracted from the NDE testing data and the critical crack size $a_c$. System failure is defined as the crack size being larger than the critical crack size, $a_c$ is expressed as $$a_c = \left[\frac{K_{IC}}{C_1 \Delta \sigma}\right]^2 \frac{Q}{\pi}, \quad (25)$$

where $K_{IC}$ is the mode-I critical stress intensity. $C_1$ and Q are defined in Eq. (22) and Eq. (21), respectively. $\Delta \sigma$ is defined as before.

The crack growth rate is mainly driven by the cyclic stress intensity range at the crack tips. The stress intensity range computation considering the crack geometry, shape, location, and interaction is $$\Delta K = \frac{MC_1}{\sqrt{Q}} F\left(\frac{a}{W}\right) \Delta \sigma \sqrt{\pi a}, \quad (26)$$

where M takes values according to Eq. (23) or E2. (24). $C_1$ and Q are defined in Eq. (22) and Eq. (21), respectively. Rearrange Eq. (1) to obtain $$dN = \frac{da}{\left[\frac{da}{dN}\right]_{cyc} + \left[\frac{da}{dt}\right]_{ave} t_h}. \quad (27)$$

Using Eq. (18) the fatigue life can be obtained by integrating Eq. (27) from $a_0$ to $a_c$ as $$N_{RUL} = \int_{a_0}^{a_c} \frac{da}{C_0 \Delta K^{n_0} + B(C_t)_{ave}^q t_h}. \qquad (28)$$

Ultrasound indication interacting and merging criteria, according to an exemplary embodiment of the present invention.

Internal cracks may propagate in the condition of high temperature and high pressure. Different from bored rotor, the solid rotor has no internal surface and thus it has no surface crack like that in the bored rotor. Internal cracks are usually located within 40% depth of the rotor radius. Therefore, no surface crack is considered in a solid rotor. Ultrasound scanning is carried out from the outside of the solid rotor and it scans around the entire core. Suspicious indications are analyzed in a data preprocessor. The data preprocessor maps indication positions to cylindrical coordinates. Given this indication information, the initial crack size for each of the indications is estimated assuming indications are circular. The interaction between two ultrasound indications is based on empirical and expect knowledge. Each pair of two indications are analyzed to determine whether they interact or not. If an indication has no interaction with other indications, it is treated as an isolated crack. If two indications interact with each other, corresponding geometry and crack shape correction factors may be used to compensate the interaction effect in the calculation of stress intensity factors. Two cracks may merge to one larger crack at some point during the process of crack propagation. The crack growth calculation based on a cycle-by-cycle method may consider those changes at each iteration. The crack growth is assumed to occur only in the r–z plane, as shown in FIG. 2.

Interaction criteria of two indications.

The interaction criteria of two indications depends on two aspects. Denote the spatial distance between two indication centers as S, where $S = \sqrt{(x_1-x_2)^2 + (y_1-y_2)^2 + (z_1-z_2)^2}$. Values $x_1, y_1, z_1$ and $x_2, y_2, z_2$ are Cartesian coordinates of the two indications. It is trivial to convert the cylindrical coordinate $(r, \theta, z)$ to the Cartesian coordinate $(x, y, z)$ using $x = r \cos(\theta)$ and $y = r \sin(\theta)$. Denote $D = \max(D_1, D_2)$ as the maximum diameter of the two indications. The first criterion for interaction is $S<3D$. Since the assumption is made that crack growth occurs only in the r–z plane, an angular separation distance limit can be imposed to limit the interactions. FIG. 2 shows the angular separation distance in the r–$\theta$ plane for two indications of length $D_1$ and $D_2$. The distance $2h = r_{ave} \Delta \theta$, where $r_{ave} = (D_1+D_2)/2$ is the average radius of the two indications and $\Delta \theta = |\theta_1 - \theta_2|$ is the angular difference of the two indications. The second criterion for interaction is $2h/D<0.8$. Given both of the criteria are satisfied, the two cracks are considered as interacting cracks in the calculation of the crack growth. The geometry interaction coefficients are calculated according to the specimens shown in FIG. 1A.

Merging of two indications.

Figure 3:
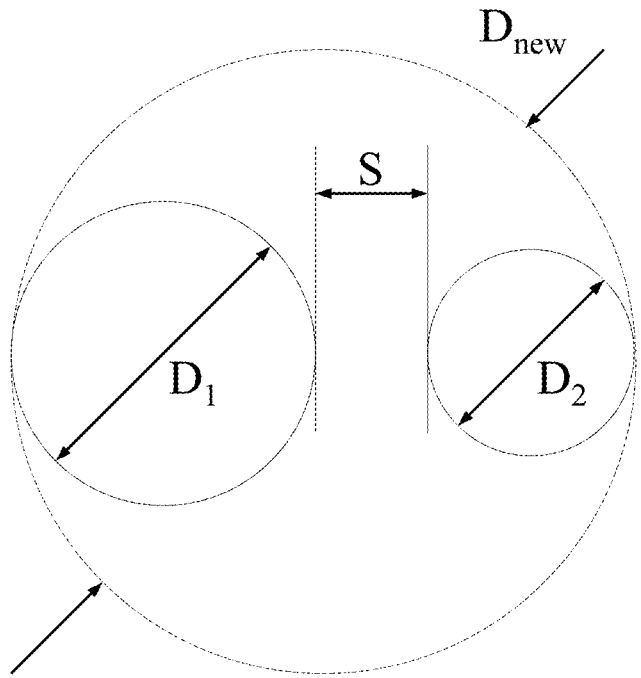
FIG. 3 is a merging illustration diagram.

Crack growth is a dynamic process. Two small isolated cracks may grow separately, interact with each other, and merge into one crack finally. Currently, the merging criterion for two interacting cracks is illustrated in FIG. 3. After two cracks merge into one crack, it is also possible this new crack with size of $D_{new}$ continues to interact or merge with another crack. Therefore, during each iteration for crack growth calculation in one cycle, all those criteria may be evaluated using new crack sizes to determine interactions and merging.

An expert system in accordance with an exemplary embodiment of the present invention.

The AutoNDE software platform is implemented using Visual Studio as a comprehensive tool for ultrasound inspection data analysis and visualization, and life prediction (see FIG. 6). AutoNDE is designed to be very flexible to be adapted to various applications. One major component of AutoNDE is data analysis and visualization, which involves transforming the raw ultrasound inspection data into human readable images. In accordance with an exemplary embodiment of the present invention, flaw area identification and grouping algorithms are integrated into AutoNDE for image analysis purposes, which are independent of the raw data. Once the components convert the raw data from ultrasound inspections and locate the flaw area, the fatigue prediction module according to an exemplary embodiment of the present invention is called by AutoNDE to finish the required computation such as fatigue crack growth trajectories and remaining useful life estimates. In accordance with an exemplary embodiment of the present invention, the interaction and merging criteria are implemented as a function in the fatigue life prediction module. Therefore, both the criteria and the module can be easily customized and used in other application scenarios.

The following is more focused on the fatigue life prediction component of the AutoNDE system shown in FIG. 7, and the details regarding the data analysis and visualization component will not be described. The overall procedure of crack growth and life calculation with interaction and merging criteria in accordance with an exemplary embodiment of the present invention is shown in FIG. 8. The basic procedure of the fatigue life prediction module is as follows: First, the critical crack size is computed based on the material information. From the loading profile specified by the user, information such as cyclic fatigue event and the creep-fatigue event is stored. Next, the program loads in NDE scan data, coverts indications to corresponding initial crack sizes, and performs interaction analysis using criteria described above under 'Ultrasound indication interacting and merging criteria.' Two NDE indications may be merged as one indication and the initial crack size of the merged indication will be recalculated accordingly. After performing preprocessing for the actual crack growth calculation, the program calculates fatigue life for each of the indications using Eq. (28) and reports results to users.

The overall procedure of fatigue life prediction is shown in FIG. 8. Step 802 reads in material properties from either direct user input or an external file stored in a computer file system. Step 803 reads in the fatigue load with temperature information from either direct user input or an external file stored in a computer file system. Step 802 and Step 803 together provide required information for Step 801 to determine the critical crack size using Eq. (25). Step 804 reads in the information on indication size, flaw location, inspection probe, and so on from a file in a computer file system. A user can also edit the file such as adding or deleting flaws manually. Step 805 uses information in Step 804 to perform the interaction and merging analysis. If the interaction of multiple indications is found, Step 806 re-evaluates the size of all interacting indications based on the largest size value of the interacting indications (e.g., the diameter D in FIG. 3). If merging criteria are met, Step 807 merges two indications into one indication and re-evaluates the indication size based on the diameter $D_{new}$ in FIG. 3. Otherwise, the indication size remains unchanged after Step 805 finishes. Step 808 uses the results of the indication size from Step 805, Step 806, and Step 807 for initial crack size calculation using Eqs. (30)-(31). The ERS in Eq. (30) is equal to the indication size (in terms of diameter). Each of the initial crack size values resulting from Step 808 will be used to calculate fatigue life. The calculation uses a cycle integration mechanism and is implemented through an iteration procedure. For each of the initial crack size values, Step 810 calculates the crack growth quantity ($\Delta a_1$) contributed by the fatigue during one load cycle, and Step 809 calculates the crack growth quantity ($\Delta a_2$) contributed by the creep during one load cycle. Step 811 obtains the crack growth quantity ($\Delta a$) during one load cycle by summing up the two components. Step 812 obtains the current crack size ($a_{N+1}$) by adding the crack growth quantity ($\Delta a$) to the crack size ($a_N$) before the load cycle and increases the fatigue life by 1 (i.e., N=N+1). Step 813 checks whether the current crack size ($a_{N+1}$) is larger than the critical crack size ($a_c$). If not, repeat Steps 809, 810, 811, 812, and 813. The iteration terminates until Step 813 identifies that the current crack size is larger than the critical crack size ($a_c$). The current value N is the fatigue life of the indication being calculated.

FIG. 14 shows three exemplary load cycles. A load cycle is characterized (at min) by the following information: minimal stress (e.g., −20 MPa), maximal stress (e.g., 500 MPa), temperature (e.g., 500 F) and holding time (e.g., 100 hours).

Examples of exemplary embodiments of the present invention.

In this section, an engineering example is used to demonstrate the overall idea of the inventive methodology of this disclosure. The procedural steps of the example are described as follows: First, ultrasound inspection data are analyzed and used to reconstruct the response image of the object. Next, the grouping algorithm is used to identify the flaws (e.g., the fatigue cracks) and a distance gain size (DGS) technique is used to estimate the size of each of the cracks. Then based on the estimation results, the fatigue life of each of the cracks is calculated using the fatigue crack growth model. The inventive interaction criteria described in this disclosure are incorporated in the calculation to include the interaction effects among multiple cracks and between the crack and boundaries. Using the fatigue life prediction results, the next inspection service interval can be recommended.

An ultrasound testing data and image reconstruction example.

The acquisition of the ultrasound inspection data is performed using appropriate equipment and software and the data are reported in RDTIFF format. The resulting data file stores all the information such as sampling frequency, sound speed in the object, probe movement, and so on. Since this example is focused on life prediction methodology, details of acquisition setup, data format, and data storage are not discussed here. Due to the fact that the movement of the probe is along the circumferential direction, the same position in the object is frequently covered by more than one response data point. Therefore, the reconstruction process uses multiple data points by taking the maximum value of the data. For example, a pixel at image coordinate (300,200) may have multiple ultrasound response data values such as 0.9, 0.8, 0.5 (normalized by 1) reported by the probe from different circumferential locations, and the maximum value of 0.9 is used in the reconstructed image. The reconstructed ultrasound response image shown in FIG. 9A and the flaw area annotated in FIG. 9B.

DGS method for fatigue crack size estimate example.

The DGS method is a graphical representation of different echo magnitudes resulting from different sizes of reflectors located at different distances from a probe. DGS diagrams have been produced for use with specific probes, one for 10 mm diameter and another for 20 mm diameter. Recent DGS diagrams are customized for individual probes and types of metal testing pieces. These diagrams may not reflect the actual sizes of flaws but they relate the flaw size to an equivalent disc size in the same way as with a calibration or comparator block, as an equivalent flaw size (EFS).

In this example, the DGS sizing formula for the used testing probe is given in Eq. (29).

$$d_1 = d_0 \sqrt{\frac{h_1}{h_0} 10^{\frac{g_0-g_1}{40}}}, \tag{29}$$

where $d_0$ is the diameter of the calibration or comparator hole, $h_0$ is the calibration intensity, $h_1$ is the maximum ultrasound inspection intensity in the flaw area, $g_0$ is the calibration gain, $g_1$ is the ultrasound inspection gain, and $d_1$ is the equivalent reflector size (ERS). In this example, the maximum intensity from inspection data is $h_1$=0.9176 (normalized by 1), the calibration intensity $h_0$=0.8, the calibration gain $g_0$=18 dB, the inspection gain $g_1$=22 dB, and the calibration equivalent reflector size $d_0$ is 2.5 mm. Using that information, the equivalent reflector size of the flaw is calculated as $d_1$=2.1 mm. The ERS is then converted to real defect size (RDS) and the RDS is used to obtain the equivalent initial flaw size (EIFS) for fatigue life prediction. The conversion from DGS equivalent reflector size to RDS is shown in Eq. (30), and the conversion from RDS to EIFS is shown in Eq. (31).

$$RDS = \begin{cases} 1.7 ERS & if ERS > 5 \\ 2.0 ERS & if ERS < 4 \\ ERS[2 - 0.3(ERS - 4)] & \text{otherwise} \end{cases} \tag{30}$$

$$a_0 = 0.5\sqrt{r}\, RDS, \tag{31}$$

where r=0.4 is the ratio of minor axis over major axis in the ellipsis-shape cracks. The EIFS of the flaw is calculated using Eq. (30) and Eq. (31) as $a_0$=1.3 mm.

Fatigue life prediction example.

In this example, creep is not considered based on the working profile of the rotor and only the cyclic fatigue crack growth model (e.g. Eq. (2)) is used. The material of this rotor is 26NiCrMoV14-5/TLV 9123 18 and the corresponding model parameters used in Eq. (2) are $C_0$=1.2604×10$^{-13}$ and $n_0$=3.1. The fracture toughness of this material is 142 MPa $\sqrt{m}$ and the critical crack size of this material is 16.3 mm. Based on the information given, the fatigue life is calculated to be 2,382 starts in total for cold, warm, and hot starts. The fatigue crack growth trajectory is show in FIG. 10. Based on the fatigue life prediction results, this rotor is re-qualified to operate about another 2,000 starts or 20,000 hours, whichever comes first.

Conclusions.

This disclosure presents an inventive fatigue life prediction methodology using ultrasound inspection data. Fatigue crack growth due to fracture mechanics and creep effects are discussed. The criteria for crack-crack interaction, crack-boundary interaction, multiple crack merging are detailed.

To demonstrate the overall inventive method, a practical engineering example is presented using ultrasound inspection data. The presented methodology and required computations are implemented as part of an expert system software platform, for example, AutoNDE. Based on the above discussion, several conclusions are drawn.

The inventive methodology can be directly applied for fatigue life prediction in industrial generator rotors for decision making. For example, based on ultrasound inspection data, the remaining useful life for a rotor can be estimated for condition-based maintenance.

The software platform AutoNDE, when embodied with the methodology of the present invention, can analyze the ultrasound inspection data and identify the flaw region, which is very efficient for large amount of data. The two dimensional (2D)/3D visualization capability of AutoNDE system can improve the overall efficiently of the inventive method.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article or manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

Referring now to FIG. 11, according to an exemplary embodiment of the present invention, a computer system 1101 can comprise, inter alia, a central processing unit (CPU) 1102, a memory 1103 and an input/output (I/O) interface 1104. The computer system 1101 is generally coupled through the I/O interface 1104 to a display 1105 and various input devices 1106 such as a mouse and keyboard. The support circuits can include circuits such as cache, power supplies, clock circuits, and a communications bus. The memory 1103 can include RAM, ROM, disk drive, tape drive, etc., or a combination thereof. Exemplary embodiments of present invention may be implemented as a routine 1107 stored in memory 1103 (e.g., a non-transitory computer-readable storage medium) and executed by the CPU 1102 to process the signal from a signal source 1108. As such, the computer system 1101 is a general-purpose computer system that becomes a specific purpose computer system when executing the routine 1107 of the present invention.

The computer system 1101 also includes an operating system and micro-instruction code. The various processes and functions described herein may either be part of the micro-instruction code or part of the application program (or a combination thereof) which is executed via the operating system. In addition, various other peripheral devices may be connected to the computer system 1101 such as an additional data storage device and a printing device.

The flowchart and block diagrams in the figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

The terminology used herein is for the purpose of describing particular embodiments only and is not intended to be limiting of the invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described to best explain the principles of the invention and the practical application, and to enable others of ordinary skill in the art to understand the invention for various embodiments with various modifications as are suited to the particular use contemplated.

What is claimed is:

1. A method for a computing machine to perform fatigue life prediction, the method comprising:
    calculating a critical crack size of an object of interest, the object being a turbine;
    identifying, by a data processor, a first flaw in the object from ultrasound data of the object of interest in non-destructive evaluation, the first flaw being a crack in the object and the ultrasound data acquired using a non-destructive evaluation probe;
    determining that the first flaw interacts with a second flaw, the first flaw is to be merged with the second flaw, or the first flaw is isolated;
    calculating an initial crack size based on the determination;
    calculating by a fatigue prediction module of a non-destructive evaluation system, an increase in the initial crack size in the object due to fatigue and creep;
    determining, by the fatigue prediction module of the non-destructive evaluation system, a number of load cycles until the initial crack size reaches the critical crack size of the object,
    wherein the initial crack size is calculated using the following equations:

$$RDS = \begin{cases} 1.7 ERS & \text{if } EFS > 5 \\ 2.0 ERS & \text{if } ERS < 4 \\ ERS[2 - 0.3(ERS - 4)] & \text{otherwise} \end{cases}$$

$$a_0 = 0.5\sqrt{r}\,RDS$$

wherein $a_0$ is the initial crack size, RDS is a real flaw size and ERS is an equivalent reflector size of the flaw, ERS being a function of a size of the probe;
    determining a fatigue life of the turbine based on the number of load cycles; and
    performing maintenance of the turbine at a service interval based on the fatigue life of the turbine.

2. The method of claim 1, wherein the object of interest includes part of a turbine generator.

3. The method of claim 2, wherein the part includes a rotor.

4. The method of claim 1, wherein the first flaw interacts with the second flaw when a predetermined criteria for interaction is met.

5. The method of claim 1, wherein the first flaw is to be merged with the second flaw when a predetermined criteria for merging is met.

6. The method of claim 1, wherein the step of calculating the increase in the initial crack size due to fatigue and creep is repeated until the initial crack size meets or exceeds the critical crack size.

7. The method of claim 1, wherein a load cycle includes a minimum stress applied to the object, a maximum stress applied to the object, a temperature exposure of the object and a holding time.

8. A system of fatigue life prediction, the system comprising:
    a memory device for storing a program;
    a processor of a non-destructive evaluation system, the processor in communication with the memory device, the processor operative with the program to:
    calculate a critical crack size of an object of interest;
    identify a first flaw in the object from ultrasound data of the object of interest in non-destructive evaluation, the first flaw being a crack in the object, and a non-destructive evaluation probe providing the ultrasound data;
    determine that the first flaw interacts with a second flaw, the first flaw is to be merged with the second flaw, or the first flaw is isolated;
    calculate an initial crack size in the object based on the determination;
    calculate an increase in the initial crack size due to fatigue and creep;
    determine a number of load cycles until the initial crack size reaches the critical crack size based on the increase, wherein the initial crack size is calculated using the following equations:

$$RDS = \begin{cases} 1.7ERS & \text{if } EFS > 5 \\ 2.0ERS & \text{if } ERS < 4 \\ ERS[2 - 0.3(ERS - 4)] & \text{otherwise} \end{cases}$$

$$a_0 = 0.5\sqrt{r}\,RDS$$

wherein $a_0$ is the initial crack size, RDS is a real flaw size and ERS is an equivalent reflector size of the flaw, ERS being a function of a size of the probe; and determine a fatigue life of the object based on the number of load cycles, the fatigue life used for a service interval to perform maintenance on the object.

9. The system of claim 8, wherein the object of interest includes part of a turbine generator.

10. The system of claim 9, wherein the part includes a rotor.

11. The system of claim 8, wherein the first flaw interacts with the second flaw when a predetermined criteria for interaction is met.

12. The system of claim 8, wherein the first flaw is to be merged with the second flaw when a predetermined criteria for merging is met.

13. The system of claim 8, wherein the processor is further operative with the program code to repeat calculating the increase in the initial crack size due to fatigue and creep until the initial crack size meets or exceeds the critical crack size.

14. A computer program product for fatigue life prediction, the computer program product comprising:
a non-transitory computer readable storage medium having computer readable program code embodied therewith, the computer readable program code comprising:
computer readable program code configured to:
calculate a critical crack size of an object of interest;
identify a first flaw in the object from ultrasound data of the object of interest in non-destructive evaluation, the first flaw being a crack in the object and the ultrasound data obtained with a non-destructive evaluation probe;
determine that the first flaw interacts with a second flaw, the first flaw is to be merged with the second flaw, or the first flaw is isolated;
calculate an initial crack size in the object based on the determination;
calculate an increase in the initial crack size due to fatigue and creep;
determine a number of load cycles until the initial crack size reaches the critical crack size based on the increase,
wherein the initial crack size is calculated using the following equations:

$$RDS = \begin{cases} 1.7ERS & \text{if } EFS > 5 \\ 2.0ERS & \text{if } ERS < 4 \\ ERS[2 - 0.3(ERS - 4)] & \text{otherwise} \end{cases}$$

$$a_0 = 0.5\sqrt{r}\,RDS$$

wherein $a_0$ is the initial crack size, RDS is a real flaw size and ERS is an equivalent reflector size of the flaw, ERS being a function of a size of the probe; and determine a fatigue life of the object based on the number of load cycles, the fatigue life used for a service interval to perform maintenance on the object.

15. The computer program product of claim 14, wherein the object of interest includes part of a turbine generator.

16. The computer program product of claim 15, wherein the part includes a rotor.

17. The computer program product of claim 14, wherein the first flaw interacts with the second flaw when a predetermined criteria for interaction is met.

18. The computer program product of claim 14, wherein the first flaw is to be merged with the second flaw when a predetermined criteria for merging is met.

19. The computer program product of claim 14, wherein calculation of the increase in the initial crack size due to fatigue and creep is repeated until the initial crack size meets or exceeds the critical crack size.

20. A method for a computing machine to perform fatigue life prediction, the method comprising:
calculating a critical crack size of an object of interest;
identifying a first flaw of the object of interest in non-destructive evaluation, the first flaw being a crack in the object, and the identifying being from data reported by a non-destructive evaluation probe;
determining that the first flaw interacts with a second flaw, the first flaw is to be merged with the second flaw, or the first flaw is isolated;
calculating an initial crack size in the object based on the determination;
calculating, by a fatigue prediction module of a non-destructive evaluation system, an increase in the initial crack size due to fatigue and creep;
determining a number of load cycles until the initial crack size reaches the critical crack size based on the increase,
wherein the initial crack size is calculated using the following equations:

$$RDS = \begin{cases} 1.7ERS & \text{if } EFS > 5 \\ 2.0ERS & \text{if } ERS < 4 \\ ERS[2 - 0.3(ERS - 4)] & \text{otherwise} \end{cases}$$

$$a_0 = 0.5\sqrt{r}\,RDS$$

wherein $a_0$ is the initial crack size, RDS is a real flaw size and ERS is an equivalent reflector size of the flaw, ERS being a function of a size of the probe;

determining a fatigue life of the object based on the number of load cycles; and performing maintenance at a service interval based on the fatigue life of the object.

21. The method of claim 20, wherein the first and second flaws are found using non-ultrasound data.

* * * * *